US 9,295,801 B2

(12) United States Patent
Graham et al.

(10) Patent No.: US 9,295,801 B2
(45) Date of Patent: Mar. 29, 2016

(54) BREATHING TUBE (75) Inventors: Peter Kenneth Graham, Auckland (NZ); Jonathan David Harwood, Auckland (NZ); Laurence Gulliver, Auckland (NZ)

(73) Assignee: Fisher & Paykel Healthcare Limited (NZ)

( * ) Notice: Subject to any disclaimer, the term of this patent is extended or adjusted under 35 U.S.C. 154(b) by 507 days.

(21) Appl. No.: 13/698,272

(22) PCT Filed: May 13, 2011

(86) PCT No.: PCT/NZ2011/000076
§ 371 (c)(1),
(2), (4) Date: Jan. 24, 2013

(87) PCT Pub. No.: WO2011/149362
PCT Pub. Date: Dec. 1, 2011

(65) Prior Publication Data
US 2013/0112201 A1    May 9, 2013

Related U.S. Application Data

(60) Provisional application No. 61/348,020, filed on May 25, 2010.

(51) Int. Cl.
*A61M 16/08* (2006.01)
*A61M 16/06* (2006.01)
(Continued)

(52) U.S. Cl.
CPC ....... *A61M 16/0875* (2013.01); *A61M 16/0057* (2013.01); *A61M 16/0666* (2013.01);
(Continued)

(58) Field of Classification Search
CPC ............... A61M 16/0486; A61M 16/1045; A61M 16/1075; A61M 16/1085; A61M 16/1095; A62B 9/003; F16L 59/06; F16L 59/07; F16L 59/153
USPC ............. 128/203.26, 203.27, 204.17, 206.22; 607/104; 604/23, 26
See application file for complete search history.

(56) References Cited

U.S. PATENT DOCUMENTS 1,596,754 A * 8/1926 Moschelle ............ A61M 27/00
604/541
3,490,496 A * 1/1970 Stearns ..................... F16L 9/18
138/112

(Continued)

FOREIGN PATENT DOCUMENTS

FR    EP 2442003 A1 *  4/2012  ............ B29C 63/42
JP    S51-84296          7/1976
(Continued)

OTHER PUBLICATIONS

International Search Report; PCT/NZ2011/000076; dated Nov. 4, 2011; 5 pages.
(Continued)

*Primary Examiner* — Tan-Uyen (Jackie) T Ho
*Assistant Examiner* — Joseph D Boecker
(74) *Attorney, Agent, or Firm* — Knobbe Martens Olson & Bear LLP (57) ABSTRACT

Condensation or "rain-out" is a problem in breathing circuits and especially neonatal breathing circuits. The subject patent provides an improved breathing tube component for managing rain-out particularly in neonatal applications. In particular the breathing tube has a smooth inner bore, and an outer insulating layer containing stagnant gas and a heater wire.

20 Claims, 4 Drawing Sheets

(51) Int. Cl.
  *A61M 16/00* (2006.01)
  *A61M 16/10* (2006.01)
  *A61M 16/16* (2006.01)

(52) U.S. Cl.
  CPC ....... *A61M16/1075* (2013.01); *A61M 16/1095* (2014.02); *A61M 16/16* (2013.01); *A61M 2205/3653* (2013.01)

(56) References Cited

U.S. PATENT DOCUMENTS

| | | | | |
|---|---|---|---|---|
| 3,867,946 | A * | 2/1975 | Huddy | A61M 16/0666 128/207.18 |
| 4,098,298 | A * | 7/1978 | Vohrer | F16L 11/112 138/122 |
| 5,357,948 | A * | 10/1994 | Eilentropp | A61M 16/08 128/203.26 |
| 5,381,511 | A * | 1/1995 | Bahar | F16L 11/12 138/104 |
| 5,600,752 | A * | 2/1997 | Lopatinsky | A61M 16/1075 138/114 |
| 6,190,480 | B1 | 2/2001 | Carlson | |
| 6,354,332 | B1 * | 3/2002 | Burkhardt | F16L 11/15 138/109 |
| 6,435,180 | B1 * | 8/2002 | Hewson | A61M 16/16 128/203.12 |
| 6,536,428 | B1 * | 3/2003 | Smith | A61M 16/08 128/203.17 |
| 6,662,802 | B2 * | 12/2003 | Smith | A61M 16/08 128/200.24 |
| 6,769,452 | B2 * | 8/2004 | Qutub | F16L 11/11 138/114 |
| 7,086,422 | B2 * | 8/2006 | Huber | A61M 16/0875 128/207.14 |
| 7,958,891 | B2 * | 6/2011 | Smith | A61M 16/08 128/201.13 |
| 8,733,405 | B2 * | 5/2014 | Goddard | F16L 9/00 138/121 |
| 9,022,036 | B2 * | 5/2015 | Graham | A61M 16/0463 128/207.14 |
| 9,113,501 | B2 * | 8/2015 | Long | H05B 3/48 |
| 2003/0028139 | A1 * | 2/2003 | Inoue | A61M 13/003 604/26 |
| 2006/0201504 | A1 * | 9/2006 | Singhal | A61M 16/00 128/204.18 |
| 2008/0091136 | A1 * | 4/2008 | House | A61M 25/01 604/23 |
| 2010/0043793 | A1 | 2/2010 | Koulechov et al. | |
| 2010/0224195 | A1 * | 9/2010 | Henry | A61M 16/0875 128/205.25 |
| 2010/0325861 | A1 * | 12/2010 | Gardner | F16L 9/147 29/428 |
| 2011/0061658 | A1 * | 3/2011 | Koorn | A61M 16/04 128/207.14 |
| 2012/0125333 | A1 * | 5/2012 | Bedford | A61M 16/06 128/203.25 |

FOREIGN PATENT DOCUMENTS

| | | | |
|---|---|---|---|
| JP | H08-109984 | 4/1996 | |
| NL | EP 2153859 A1 * | 2/2010 | ........ A61M 16/0816 |
| WO | WO 2007/045928 | 4/2007 | |
| WO | WO 2009/092057 | 7/2009 | |

OTHER PUBLICATIONS

Written Opinion; PCT/NZ2011/000076, dated Nov. 4, 2011; 7 pages.
GB Examination Report; Jul. 7, 2014; 2 pages.
Examination Report for Japanese Application No. 2013-512562, dated Jan. 28, 2015, 4 pages.

* cited by examiner

Figure 1

(PRIOR ART)

BREATHING TUBE

CROSS-REFERENCE TO RELATED APPLICATIONS

This application is a national phase of International Application No. PCT/NZ2011/000076, filed May 13, 2011, which claims priority from U.S. Provisional Application No. 61/348,020, filed May 25, 2010.

BACKGROUND OF THE INVENTION

1. Field of the Invention

The invention relates to breathing tubes and in particular to heated breathing tubes for use in delivering breathing gases to a patient. In a more particular aspect the invention relates to a heated inspiratory breathing tube for neonatal breathing applications.

2. Description of the Related Art

In assisted breathing, gases having elevated levels of relative humidity are supplied to, (and returned from) a patient (via a patient interface) through flexible breathing tubes of a relatively restricted size typically between a range of approximately 3 mm to 30 mm diameter (range covering both neonatal and adult applications). Such breathing tubes are ideally very light, resistant to kinking or pinching but also very flexible to ensure the greatest performance and level of comfort for the patient. The light weight of a breathing tube is very important to reduce any forces applied to the patient interface by the weight of the tube.

Various patient interface components may be used as appropriate for the type of breathing assistance required for different patients. For example, nasal cannula, nasal prongs, oral nasal masks, ET tubes, full face masks, or nasal pillows etc. The suitable choice will depend on various parameters associated with the type of treatment, such as the required gases flow rate, supplemental gases delivery, interface seal requirements, and/or therapy pressure for example.

Nasal cannulae may be used for example, in circumstances where a patient is breathing normally, or requires supplementary gases such as oxygen. These devices are typically supplied by a double entry lumen of small diameter (2-3 mm range) that attaches to a breathing tube. The small lumen tubes supply both sides of the nasal cannula and provide even airflow to each nasal prong. These devices have worked well for gas flows of between 0 to 5 liters per minute and have been well received by patients over the last 30 years. With patient interfaces such as nasal cannulae the stability of the nasal prongs on the face is very important, as movement of the prongs within the nares can cause severe irritation.

The new application of Humidified High Flow Nasal Cannula (HHFNC) extended therapies generally result in a nasal cannula reaching temperatures in excess of 35 degrees C. and flow rates of up to approximately 10 liters per minute for infants, up to approximately 20 liters per minute for pediatric applications and up to approximately 60 liters per minute (for adults).

Supplementary oxygen (if required) is generally supplied as a dry gas, but it is known to be beneficial to either heat and/or humidify gases before delivering them for breathing by a patient.

It is also known to be beneficial and therapeutic to supply an individual with a sufficient amount of respiratory airway pressure in order to maintain a minimum level of air volume in the lungs. Hence, the application of such sufficient pressure, called continuous positive airway pressure (CPAP), has been found to be advantageous in maintaining a minimum air volume or lung pressure when an individual is spontaneously breathing. CPAP can be supplied through nasal attachment devices, face masks, or endotracheal devices.

In the above therapies, breathing gases inhaled by a patient are preferably delivered in a condition having humidity near saturation level and at close to body temperature (usually at a temperature between 33° C. and 37° C.). Condensation or rain-out can form on the inside surfaces of the inspiratory breathing tube as the high humidity breathing gases cool and/or come into contact with the relatively cooler breathing tube surface. Condensate forming in a breathing tube can pool within the tube and be breathed or inhaled by a patient and may lead to coughing fits, choking or other discomfort. For neonatal applications in particular, mobile condensate is especially detrimental, and it is desirable to reduce mobile condensate as much as possible. Condensate within a breathing tube may also interfere with the performance of connected equipment and ancillary devices, filters and/or various sensors.

Figure 1:
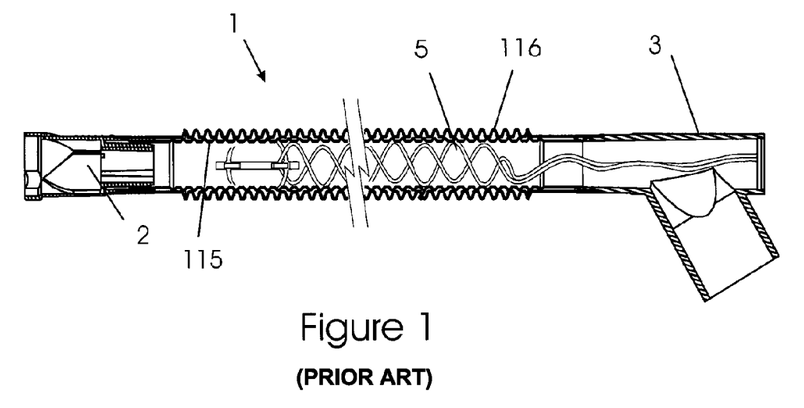
FIG. 1 is a side view of a typical insulated annular corrugated breathing tube with internal heater wire.

Attempts have been made to reduce the adverse effects of mobile condensate by either reducing the level of condensation forming, or providing collection points for draining condensed liquid from the tubing component. Reducing the condensation or rain-out forming has generally been achieved by maintaining or elevating the temperature above the dew point temperature of the breathing gas. This temperature is typically maintained by a heater wire arranged within the breathing tube (as shown in FIG. 1) in the path of flowing breathing gases, although the rain-out performance of these breathing tubes often may not be complete due to a number of factors. With reference to FIG. 1, a typical heated medical corrugated breathing tube 1 comprises an inner tube, and an outer tube and includes end connector fittings 2,3 of a standard type (moulded plastic) according to the intended use of the medical tubing and may incorporate an internal medical taper for example. The end connectors 2,3 may also include additional ports for receiving sensors and the like. End connector 3 (humidifier end) also includes a connection (not shown) for delivering power to the heater wire 5. Breathing tube 1, comprises one corrugated tube 115 within another corrugated tube 116, defining an insulation space between the tubes to improve rain-out performance.

Particularly, in 'single use' or short term use applications such as typically found in a hospital environment, the manufacturing cost of breathing tubes is especially important. It is highly desirable to even further reduce or eliminate mobile condensate, while preferably also maintaining a low production cost.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to provide a breathing tube that will at least go some way towards improving on the above or which will at least provide the public and the medical profession with a useful choice.

In a first aspect the invention consists in a breathing tube comprising: a first inner tube defining a breathing gases passage having a smooth inner surface, a second outer tube surrounding said first tube and defining a space between said first tube and said second tube, and a heater located outside said inner surface of said inner tube and in contact with said inner tube at a plurality of locations, and wherein said space includes insulation comprising a substantially stagnant gas.

Preferably said substantially stagnant gas is at least substantially sealed within said space.

Preferably said substantially stagnant gas does not flow through said space at a rate greater than 0.3 L/min.

Preferably said heater comprises at least one heater wire wrapped around the outside of said inner tube.

Preferably wherein said heater comprises a heater wire embedded in the wall of said inner tube.

Preferably said heater comprises at least one heater wire with a first end and a second end, and said at least one heater wire is arranged in an electrical loop such that said first end, and said second end, are located at the same end of said breathing tube.

Preferably said loop comprises two heater wires electrically connected at the loop end.

Preferably said heater wire extends substantially the entire length of said breathing tube.

Preferably said heater wire is arranged helically with respect to the axis of said inner tube.

Preferably said helically arranged heater wire is arranged to have a varying helical pitch, along the length of said breathing tube.

Preferably said heater wire is arranged parallel with respect to the axis of said inner tube.

Preferably said second outer tube is independently formed and separate from said inner tube, and wherein said inner tube lies freely within said outer tube along a non-tortuous path.

Preferably said second outer tube is a corrugated tube.

Preferably said corrugated outer tube is an extruded tube having a corrugation profile comprising alternating outer crests and inner troughs and a substantially uniform wall thickness.

Preferably said corrugated outer tube is a spirally wound tube having helical reinforcing bead corrugations.

Preferably said insulation in said space further comprises an insulating material such as wool, glass or mineral fibres, insulating gas or fluid, foamed or expanded polymer.

Preferably said stagnant gas is air.

Preferably said first inner tube includes at least one helical bead on said smooth inner surface.

Preferably said first inner tube includes at least one helical bead on the outer surface.

Preferably said first inner tube is a spirally wound tube having a helical bead on the outer surface.

Preferably said heater comprises at least one heater wire wrapped around the outside of said inner tube between said helical bead.

Preferably the pitch of said helical wire is variable along the length of said breathing tube.

Preferably said inner wall of said inner tube further comprises a plurality of ribs arranged about the circumference of said inner tube and generally aligned with the longitudinal axis of the inner tube.

Preferably there are 2 to 8 said ribs.

Preferably there are 3 to 5 said ribs.

Preferably said outer wall of said inner tube further comprises a plurality of ribs arranged about the circumference of said inner tube and generally aligned with the longitudinal axis of the inner tube.

Preferably there are 2 to 8 said ribs.

Preferably there are 3 to 5 said ribs.

Preferably a first end of said breathing tube includes a first end connector and a second end of said breathing tube includes a second end connector, and each of said first and second end connectors includes an annular recess that receives and substantially seals an end of said inner tube, and each of said first and second end connectors includes a gases pathway therethrough fluidly connected with a respective end of said inner tube.

Preferably each of said first and second end connectors further receives an end of said outer tube.

Preferably at a first end of said breathing tube said heater passes through the wall of said inner tube and into said gases pathway through said first end connector and is electrically connected to a termination associated with a wall of said first end connector.

Preferably said heater is not exposed to said breathing gases passage at any point along said breathing tube.

Preferably said heater is routed through said first end connector in a channel and is electrically connected to a termination associated with a wall of said first connector.

Preferably said termination is at least one electrical contact supported in said wall of said first end connector and said contact is accessible from the outside of said breathing tube.

Preferably said inner tube has an inner diameter of between 3 mm and 15 mm.

Preferably said inner tube has an inner diameter of between 6 mm and 10 mm.

Preferably said inner tube has an inner diameter of between 7 mm and 9 mm.

Preferably said inner tube has an inner diameter of between 15 mm and 30 mm.

Preferably said inner tube has an inner diameter of between 16 mm and 25 mm.

Preferably said breathing tube is an inspiratory breathing tube.

Preferably said breathing tube is part of a respiratory therapy system for delivering high flow therapy to an infant patient up to 10 L/min.

Preferably said breathing tube is part of a respiratory therapy system for delivering high flow therapy to an adult patient up to 60 L/min.

In a further aspect the invention consists in a method of delivering high flow therapy to an infant patient of up to 10 L/min through a breathing tube.

In a further aspect the invention consists in a method of delivering high flow therapy to an adult patient of up to 60 L/min through a breathing tube.

Preferably said helical bead has a "loose" pitch so that the bead or beads do not significantly disrupt gases flow within said inner tube.

Preferably said inner surface does not include any of: a) ribs, b) corrugations, c) cavities, d) bumps, or e) features that disrupt gases flow.

In a further aspect the invention consists in a breathing tube as herein described with reference to any one or more of FIGS. 3 to 7.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

Unless otherwise indicated, the term "substantially" means "to a great extent" or "for a least the most part".

The invention consists in the foregoing and also envisages constructions of which the following gives examples only.

DETAILED DESCRIPTION OF THE PREFERRED EMBODIMENT

In the particular field of neonatal breathing circuits, pooled mobile condensate in the inspiratory breathing tube is especially detrimental, and it is highly desirable to reduce mobile pooled condensate to an even lower level than can be tolerated in adult applications.

There are also other requirements that should be satisfied by breathing tubing in the field of the present invention. For example, it is desirable that breathing tubes for breathing circuits are: resistant to crushing, resistant to restrictions in flow when bent (increased resistance to flow<50% when bent around a 1 inch cylinder), resistant to changes in length/volume under internal pressure (compliance), resistant to leaking (<25 ml/min @ 6 kPa), have low flow resistance (increase in pressure @ max. rated flow<0.2 kPa), electrically safe i.e.: sparks in the tubing can be extremely dangerous, especially in oxygen-rich environments such as oxygen therapy.

International standard ISO 5367: 2000(E) (Fourth ed., 2000-06-01) is an example of how some of these desirable parameters can be measured and assessed, and the document is hereby incorporated into this specification in its entirety by reference. Components of the invention should meet or exceed these standards which distinguish breathing tubes in the field of the invention from other types of tubing not suitable for medical use as a breathing tube.

In this specification, terms "medical circuit" and "breathing circuit" are used to indicate the general field of the invention. It is to be understood that a "circuit" is intended to include open circuits, which do not form a complete closed circuit. The term "breathing circuit" is intended to include such "open circuits". Similarly, the term "breathing tube" is intended to be read as flexible tubing suitable for use in the type of breathing circuits described above for connecting and providing a breathing gases pathway between components of a breathing circuit.

Neonatal Breathing Tubing

In one particular embodiment, medical tubing in the field of the present invention has a nominal bore size from approximately 3 mm to approximately 15 mm, and lengths ranging from approximately 300 mm to 2.5 m.

Figure 2:
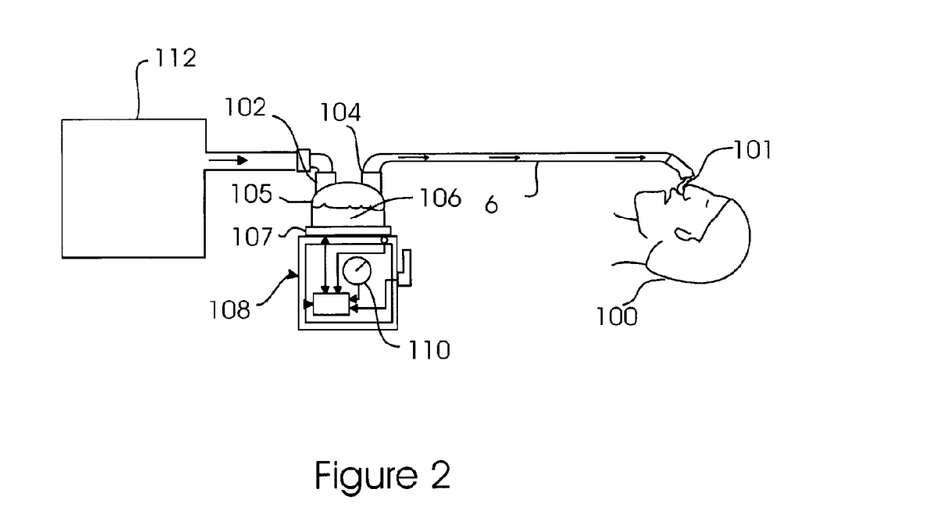
FIG. 2 is a schematic illustration of one type of breathing circuit in which a breathing tube according to the invention can be used.

With reference to FIG. 2 a humidified ventilation system is shown in which a patient/infant 100 is receiving humidified and pressurised gases through a patient interface 101 (e.g. nasal cannula) connected to a humidified gases transportation pathway or inspiratory breathing tube 6. It should be understood that delivery systems could be continuous, variable or bi-level positive airway pressure or numerous other forms of respiratory therapy. The inspiratory tube 6 is connected to the outlet 104 of a humidification chamber 105 which contains a volume of water 106. The inspiratory tube 6 may contain a heater (not shown) which heats the walls of the tube to reduce condensation within. The humidification chamber 105 is preferably formed from a plastics material and may have a highly heat conductive base (for example an aluminium base) which is in direct contact with a heater plate 107 of humidifier 108. The humidifier 108 is provided with control means or electronic controller which may comprise a microprocessor based controller executing computer software commands stored in associated memory.

In response to the user set humidity or temperature value input via dial 110, for example, and/or other inputs, the controller determines when (or to what level) to energise heater plate 107 to heat the water 106 within humidification chamber 105. As the volume of water 106 within humidification chamber 105 is heated, water vapour begins to fill the volume of the chamber above the water's surface and is passed out of the humidification chamber 105 outlet 104 with the flow of gases (for example air) provided from a gases supply means or ventilator/blower 112 which enters the chamber through inlet 102. Exhaled gases from the patient's mouth are passed directly to ambient surroundings in FIG. 2.

It will be appreciated the patient interface 101 could equally be a nasal mask, oral mask or full-face mask.

Figure 3:
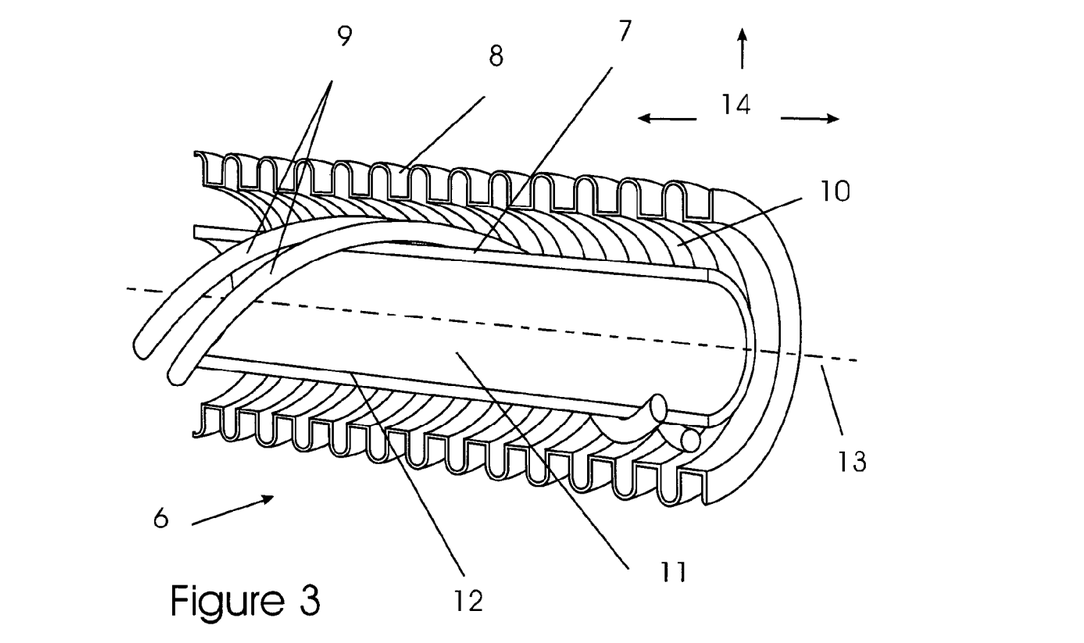
FIG. 3 is a cross section view of a breathing tube according to one embodiment including a looped heater wire.
Figure 4:
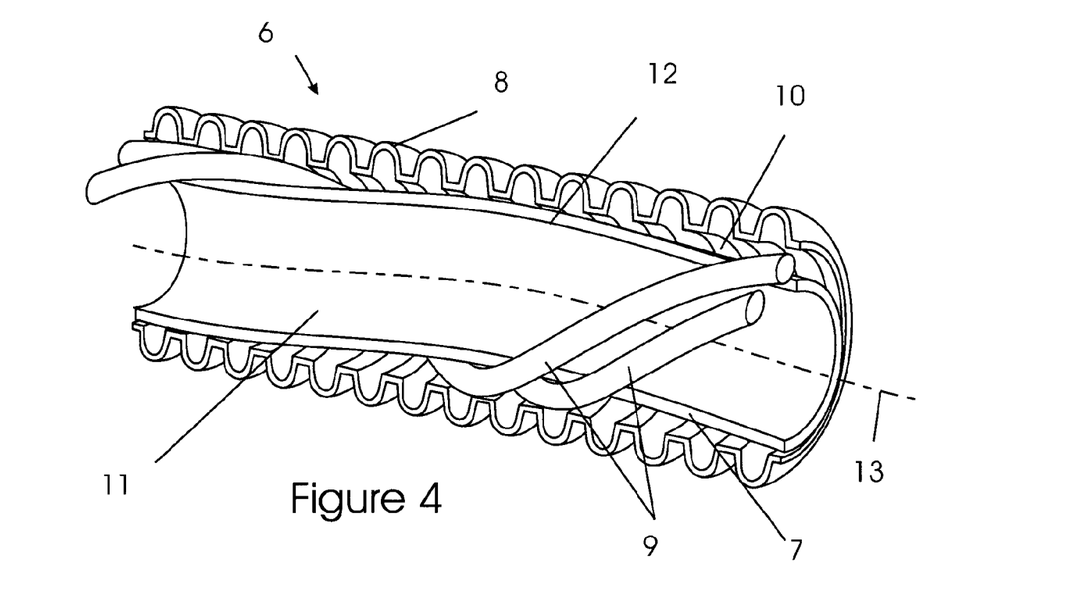
FIG. 4 is a cross section view of the breathing tube of FIG. 3 showing movement of the separate inner tube within the outer tube.

With particular reference to FIGS. 3 & 4, the detailed structure of a preferred inspiratory breathing tube will be described. Breathing tube 6 comprises inner tube 7 having a smooth inner wall surface 12 that defines a breathing gases passageway 11 for delivering breathing gases to a patient.

The term "smooth" is used to describe tubes that have an inner surface that does not include inner corrugations or annular ribs, or bumps or cavities that significantly influence the flow of gases along the tube. Inner tube 7 is surrounded by a separate outer tube 8, which is corrugated as shown in FIGS. 3 & 4. The arrangement of the inner tube 7 with respect to outer tube 8 is substantially co-axial i.e. the longitudinal axis 13 of inner tube 7 is approximately co-axial with the axis of outer tube 8, and inner tube 7 lies freely within tube 8 along a non-tortuous path. It will be appreciated that the arrangement illustrated in FIG. 4 is intended to be an example of what is to be considered substantially co-axial, that is the axis of inner tube 7, and tube 8, are generally aligned. Due to both the inner tube 7, and tube 8, being flexible their respective axes are likely to not be straight lines and not perfectly aligned along the entire length.

The arrangement of the separate inner tube 7 within the outer tube 8 defines a space 10 which insulates the inner tube 7 from the ambient surroundings 14. The present application is typically in a hospital environment which is commonly an air conditioned environment and/or quite drafty which can lead to relatively cool ambient conditions surrounding the breathing circuit and exacerbate rain-out. Space 10 preferably contains a substantially stagnant gas, typically air. Alternatively space 10 may be sealed and filled with a gas e.g. air or nitrogen etc. In a further alternative embodiment, space 10 may also include an insulation material such as wool, glass or mineral spun fibres, insulating fluid, foamed or expanded polymer insulating material. It is intended that any significant fluid or gas flow in space 10 is not considered to be "stagnant gas". Gases movement due to natural convection are considered substantially "stagnant". The term "substantially stagnant gas" includes non-forced gases, and/or gases flowing through space 10 having a flow rate less than 0.3 Liters per minute (L/min).

Inner tube 7 further includes a heater located outside the smooth inner surface 12, and preferably extends substantially the entire length of breathing tube 6. The heater is in direct contact with inner tube 7 at a plurality of locations along a heating length of the breathing tube. As shown in FIG. 3, the heater comprises a pair of heater wires 9 wound around the outside of inner tube 7 in a helical configuration. As a result of this arrangement and the direct contact between heater wires 9 and the wall of the inner tube 7, the tube wall can be efficiently and evenly heated, thereby reducing formation of condensate. By heating the tube directly, the tube wall can be maintained at a temperature higher than the breathing gases in the tube. The thermal gradient (from high to low temperature) is from the outside of the tube, through the wall and into the gases in the tube. This arrangement has found to be significantly better (for reducing rainout) than an inspiratory breathing tube containing a heater wire located in the inspiratory gases flow.

In an internally heated arrangement (such as shown in FIG. 1), the heater wire heats the gases flow which then in turn heats the tube wall. This arrangement results in a thermal gradient where the lowest temperature exists at the wall of the tube thereby resulting in poorer rainout performance.

It is preferable that the heater wire 9 is formed in a loop so that the electrical circuit starts and finishes at the same end of the breathing tube 6, which can be attached to a respiratory device that provides power to the heater wire circuit. Alternatively, heater wires 9 may be two separate runs of heater wire that are subsequently joined at the patient end of breathing tube 6. Attachment of electrical termination connectors and/or joining of the ends of the wires to create a return loop (or loops if multiples are desired) could be performed in a number of ways. These could include soldering, crimp connection, insulation displacement connection (IDC) and resistance welded joints. These connection methods can be implemented in various ways to achieve parallel, series or combinations of these methods depending on the desired result.

In alternative embodiments, the heater wire(s) 9 may be embedded in the wall of inner tube 7 and arranged helically with respect to the axis 13 of inner tube 7, or arranged substantially parallel with respect to axis 13.

Inner tube 7 includes a smooth inner wall 12 and may be formed as a circular extrusion. Alternatively, smooth inner wall tube 7 may include a number of substantially longitudinal (i.e. aligned substantially parallel with the axis of inner tube 7) ribs on the interior surface which function to prevent blockages in passageway 11 if the breathing tube 6 is bent. Such ribs are considered to not have a significant effect on gases flow because they extend at least for the most part in a direction aligned with the flow. For example, the inner tube 7 may include 3 to 8 anti-kinking ribs, which may be arranged regularly around the circumference.

Figures 7A, 7B:
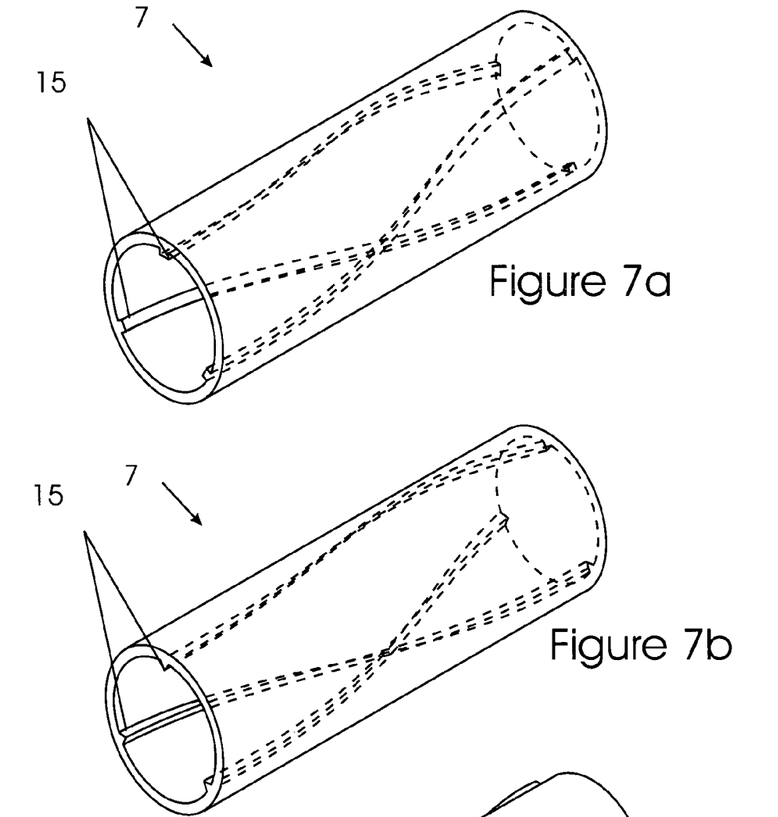
FIG. 7 is a schematic view of different wall section configurations of the inner tube.

Alternatively, with reference to FIGS. 7a and 7b, the inner surface may include helical ribs 15 having a "loose" pitch which does not significantly disrupt flow.

Alternatively, inner surface does not include any features that significantly disrupt gases flow, e.g.: corrugations, beads, ribs, or protrusions or cavities.

Figure 7C:
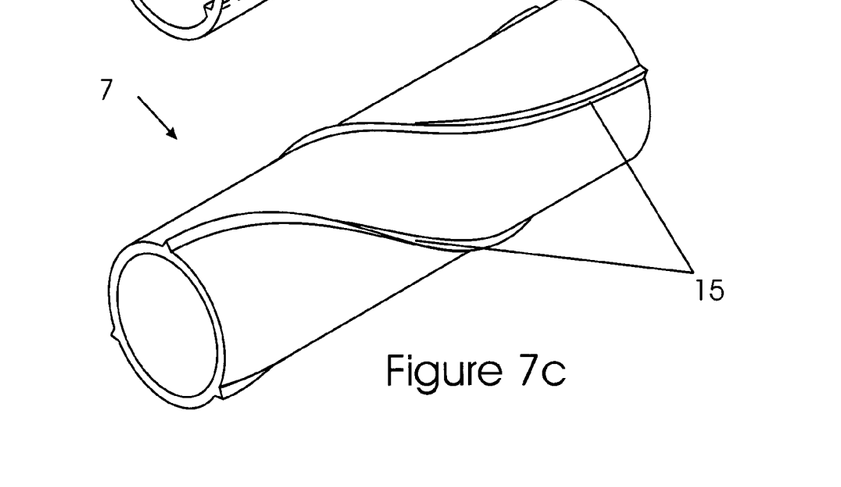

Alternatively or in addition, the outer surface of inner tube 7 may include similar anti-kinking ribs 15, as shown in one example in FIG. 7c. In this embodiment, a helical heater wire(s) may be wrapped around inner tube 7, and be located between helical ribs 15. Alternatively, the outer surface of inner tube 7 may include a number of ribs substantially parallel with the inner tube axis.

In a still further embodiment, inner tube 7 may include longitudinal or helical grooves (not shown) in the outer surface to accommodate and/or locate heater wire(s) within.

It has been found that the above described breathing tube arrangement has a significant performance advantage with respect to the formation of pooled mobile condensate. In the particular case of breathing tubes suitable for neonatal care applications (i.e. breathing tubes with breathing gases passage (11) with a diameter of between approximately 3 mm and 15 mm), the performance is particularly good. For example, tests have shown that the amount of accumulated pooled condensate in a typical tube (such as that illustrated in FIG. 1) can result in 4-5 times the accumulated pooled condensate, compared to a breathing tube configured according to the present invention (ID of approximately 8 mm). The smooth inner wall 12 of inner tube 7 functions by allowing any small condensation droplets that do form on the wall to be driven down passage 11 by the flow of breathing gases. It has been found that this effect can substantially reduce pooling of condensation droplets, and that very small entrained water droplets pose less risk and are more manageable than a large volume of liquid water or lavage, for patients including newborn infants.

Further, the substantially stagnant gas in space 10 between the inner tube 7 and outer tube 8 forms an effective insulation barrier between ambient conditions outside the tube, and the relatively warm and humid breathing gases flow within the passage 11. When coupled with efficient heating of the inner tube 7, via heater wires 9 being in substantial contact with the tube (i.e. at a plurality of locations), the performance of this breathing tube configuration against pooled mobile condensate is greatly improved over known configurations where an internal heater wire is employed in the gases stream.

It has been found that the combination of the above described features of substantially stagnant gas insulation, direct inner tube wall heating (out of the gases flow), and smooth inner tube wall, result in a breathing tube having particularly good rainout performance. Further, it has been found that the described construction is particularly suitable for neonatal applications. These breathing tubes have a performance level previously unobtainable (i.e. when the inner diameter of the inner tube is less than 15 mm) the result is a breathing tube having very good rain-out performance while maintaining a sufficient flexibility to be ideal for neonatal applications. Importantly, at the same time the cost of manufacture is only modestly increased compared with the significant performance improvement. This feature allows a breathing tube to be manufactured at a cost suitable for 'single use' applications. In a more particular neonatal embodiment, the inner diameter is restricted to no more than 10 mm, and the resulting tube may be even lighter, less bulky and more flexible, and more suitable for neonatal applications.

In one particularly important embodiment, the outer tube 8 is an extruded corrugated tube having alternating outer crests and inner troughs as shown. This type of tubing is economical to manufacture and has a substantially uniform wall thickness (i.e. location of maximum outside diameter corresponds to location of maximum inside diameter) with corrugations that provide excellent flexibility and kink resistance. In an alternative embodiment, a corrugated tube without a substantially uniform wall thickness i.e. having corrugation beads may be preferred. In a still further alternative an outer tube 8 formed from a spirally wound material may be used.

It has been additionally found that the breathing tube arrangements described are especially effective when used for high-flow therapies (HHFNC). The combined effect of High Flow Therapy with the present breathing tube construction results in a significantly improved rain-out performance, while maintaining a relatively low cost. This combination has previously been unobtainable.

End Connectors

The end connector fittings 2, 3 of the breathing tube 6 are preferably of a standard type (moulded plastic) according to the intended use of the tube (for example, the end connector may incorporate an internal medical taper). Connector fittings 2, 3 are preferably permanently fixed and/or air tight by friction fit, adhesive bonding, over moulding, or by thermal or ultrasonic welding etc.

Figure 5:
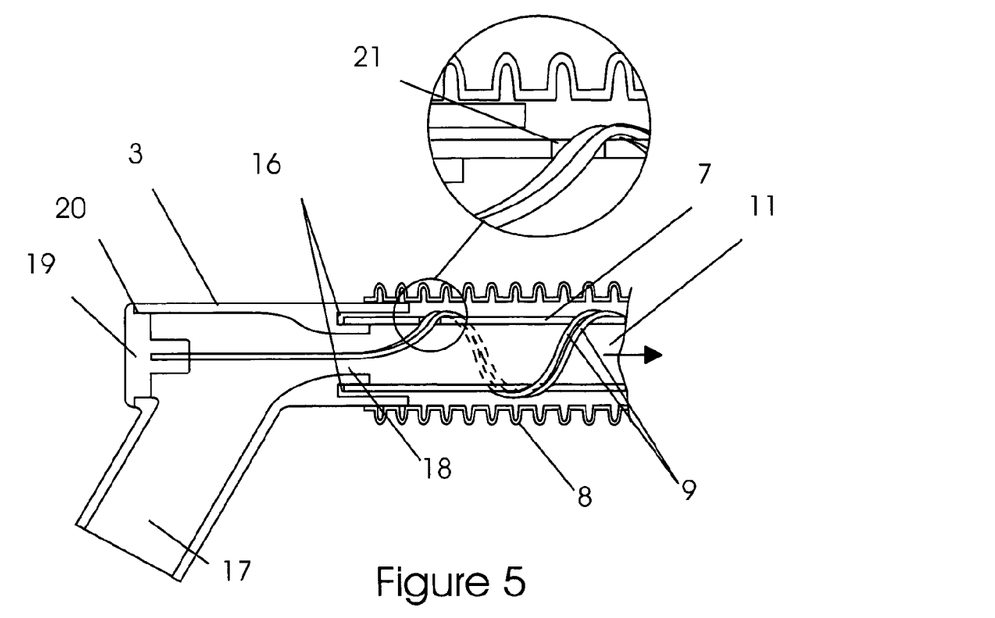
FIG. 5 is a cross section view of an end connector (chamber end) according to one embodiment showing the heater wire path through the breathing tube and end connector.

With particular reference to FIG. 5, one preferred chamber end connector 3 will be described. Connector 3 includes an inlet 17 and an outlet 18. Connector 3 further includes annular recess 16 adapted to receive inner tube 7, and thereby form a hermetically sealed connection between outlet 18 and passageway 11. Between inlet 17 and outlet 18, is a fluid pathway allowing the passage of breathing gases through connector 3 into inner tube 7. The exterior surface of connector 3 is configured to receive outer tube 8. The connection between the outer surface of connector 3 and outer tube 8 may be airtight or alternatively may be at least partially open to ambient conditions resulting in a substantially stagnant gas in space 10.

Heater wire(s) 9 are arranged outside of the interior surface of inner tube 7 along the heating length of the tube. The heater wire is therefore out of the gases pathway for almost the entire length of the tube. This has a number of significant advantages: reducing flow disruption, reducing rain-out by direct wall heating, reducing corrosion of the heater wire from contact with high humidity gas, thereby improving the in-use product life, significantly increasing safety, because any electrical faults that might cause sparks/smoke for example are outside the breathing gases flow (which may be high in O2 content.

In a region near end connector 3, heater wire(s) 9 pass through the wall of inner tube 7, into passage 11, and through connector outlet 18 before terminating at respective electrical contacts formed on a plug 19. Plug 19 is adapted to fit within aperture 20 in the wall of connector 3. Preferably the electrical contacts (not shown) are accessible from outside the breathing tube. Preferably heater wire(s) 9 pass through an aperture 21 in inner tube 7 that is hermetically sealed around the heater wires.

Embodiments of breathing tube in which all of the ends of the heater wire(s) 9 are located at one end of the breathing tube (i.e. where the heater wire electrical circuit(s) start and finish at one end), the end connector 2 can be of a standard type, requiring no accommodation of the heater wire. During assembly, it is envisaged that the heater wire be connected to the plug 19 and the plug inserted in the end connector first. The spiral wrapped heater wire can then be tightened on the inner tube so that any excess heater wire length is removed, resulting in a relatively direct path from the plug to the aperture 21 as shown. Once the heater wire 9 is tightened in position, it can be finally anchored (for example to the outside of tube 7) somewhere toward the patient end.

Figure 6:
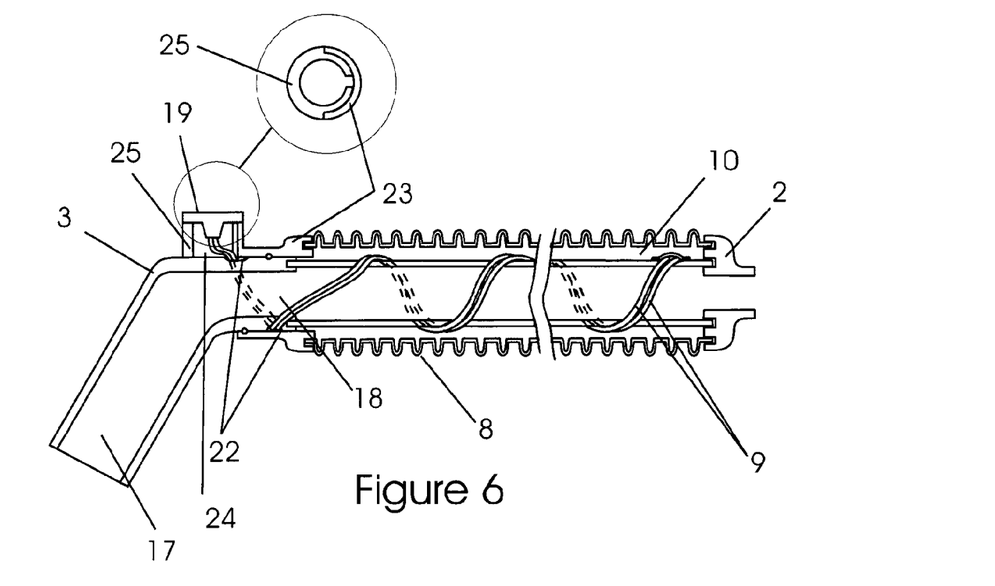
FIG. 6 is a cross section view of an end connector (chamber end) according to another embodiment showing the heater wire path through the breathing tube and end connector.

With particular reference to FIG. 6, an alternative preferred end connector arrangement wherein the heater wire 9 remains outside of the gases pathway along the entire length of the breathing tube will be described. In contrast to the previously described end connector arrangement, the heater wires 9 do not pass into the inner tube 11, but are routed through channels 22 in the end connector body. Channel 22 extends into space 24 defined by a port 25 on the end connector body 3. The heater wires are routed from the space 10 (between the inner tube 7 and outer tube 8) into port space 24 via channels 22 and a slot in the wall of port 25 (as shown in the enlarged plan view). Plug 19 forms a cover for space 24 closing port 25. It is to be understood that port 25 does not extend into the gases flow passage 11 in this embodiment. Sleeve 23 is provided over top of the outlet end of end connector 3, to cover channels 22 and receive outer tube 8 thereby sealing insulation space 10. At the patient end of the breathing tube (near end connector 2) the heater wire(s) are anchored to the outside surface of the inner tube via a suitable method e.g. adhesive tape, glue, welding or a clip. Alternatively, the patient end of the heater wire may be anchored to end connector 2. In this embodiment, plug 19 is relocated so that heater wires 9 can be routed through channels 22 and into plug 19, while remaining entirely out of the gases pathway through the end connector and inner tube 7. During assembly, heater wire 9 and plug 19 are fitted into port 25. The heater wire is routed through channel 22 and any excess heater wire length is pulled through and wound around inner tube 7 as shown. The heater wire can then be anchored to an appropriate structure such as the outer surface of the inner tube as shown in FIG. 6, before final assembly of end connector 2.

Alternative Heater Wire Arrangements and Methods

In a further embodiment, the helically arranged heater wire(s) may have a varying pitch along the length of the breathing tube. This results in varying heating density along the tube thereby allowing more or less heat to be applied to different regions of the tube that need it most. For example the chamber end where typically the highest rainout occurs for an inspiratory breathing tube. This is because the gas is typically fully saturated at the chamber outlet. The inspiratory tube is heated to increase the gas temperature inside the tube, thereby decreasing the relative humidity (and potential for rainout) of the gas as it flows towards the patient end.

In a further alternative embodiment heater wires 9 may be configured in multi-helix arrangements. A multi-helix arrangement will reduce the time required to wind the heater wires during manufacture. A further, benefit arises by increasing the number of breathing tubes (continuous production length) that can be produced before changing reels of heater wire. These benefits directly enhance the throughput of each production line.

The winding process can be performed in a number of ways depending on the desired connection devices and tube handling method(s).

Pre-Looped Spiral Heating Filament.

In this embodiment, the wire(s) is (are) pre-loaded onto an accumulator system and doubled over complete with a loop in the middle. The wire loop(s) is (are) then wound onto the tube.

Paired Heating Filaments with Joints at the Patient End.

In this embodiment, the patient end of pairs of wire strands are joined together and may require further securing with for example, hot melt glue or UV curing adhesive. A winder then rotates around the tube and applies paired runs of wire from separate spools at the same time, according to the number of wire pairs to suit the number of helixes per pitch and the desired wire arrangements. The wires may also require securing with for example hot melt glue or UV curing adhesive for example. The outer tube is subsequently fitted, and then the tubes are secured into the end connectors. Finally, the electrical end terminations are completed.

In a further embodiment it is envisaged that the helical heater wires may also carry signals for sensing devices located somewhere along the tube i.e. temperature, humidity, flow or pressure sensors. This would remove the need for a separate internal or external sensing device cables thereby reducing complexity of setup and associated clutter around the patient. Alternatively, additional winds of wire may be included for this purpose.

Rain-Out Performance

A dry 1.8 m tubing set was weighed and then set up on a Fisher and Paykel Healthcare MR850 humidification system in a temperature controlled environmental chamber set to 18° C. The MR850 system was allowed to control normally to a chamber temperature of 37° C. and an end of hose temperature of 40° C., at a constant flow rate of 5 liters per minute.

The test was run for 24 hours after which the tubing was removed and weighed to measure the amount of condensate that had accumulated within the breathing tube.

For comparison, a typical breathing tube such as that illustrated in FIG. 1 and an improved breathing tube were tested according to the experimental method described above. The table below shows the resulting pooled condensate accumulated in the breathing tubes. It can be seen that the improved breathing tube construction resulted in a significantly reduced accumulation of condensate within the breathing tube.

| Description | Length (m) | Condensate in tube (24 hr period @18° C.) (ml) | Flow (L/min) | Inner tube diameter (mm) |
| --- | --- | --- | --- | --- |
| Breathing tube of FIG. 1. (Corrugated inner and outer tube, spiral heater within inner tube) | 1.8 | 18.2 | 5 | 11 |
| Improved breathing tube (Corrugated outer tube, smooth inner tube with heater outside gas flow) | 1.8 | 4.1 | 5 | 8 |

Adult Breathing Tubing

In another particular embodiment, medical tubing of the present invention has a nominal bore size from approximately 15 mm to approximately 30 mm, and lengths ranging from approximately 300 mm to 2.5 m.

In this alternative embodiment, the structure of the adult breathing tube is substantially the same as that described for the smaller neonatal embodiment but with an increased diameter of the inner tube 7, and outer corrugated tube 8. It is difficult to produce medical tubing in the configuration described having components in this adult size range while maintaining the necessary flexibility, resistance to flow, and ability to resist kinking necessary to pass the minimum standards of a breathing tube. Careful choice of wall thickness, material, and anti-kink features are necessary to produce the required tubing in the described configuration.

An extruder 16 such as a Welex extruder equipped with a 30-40 mm diameter screw and typically a 10-13 mm annular die head with gap of 0.5-1.0 mm is suitable for producing low cost tubes quickly. Similar extrusion machines are provided by American Kuhne (Germany), AXON AB Plastics Machinery (Sweden), AMUT (Italy), Battenfeld (Germany and China). Preferred materials for manufacturing the medical tubing of the invention are Linear Low Density Polyethylene (LLDPE), Low Density Polyethylene (LDPE), Polypropylene (PP), Polyolefin Plastomer (POP), Ethylene Vinyl Acetate (EVA) or blends of these materials. Plasticised PVC may also be a suitable material, but it is not as well accepted for environmental reasons.

Preferred materials for the heater wires are copper, aluminium or a PTC (positive temperature coefficient) type material. Aluminium is not as conductive as copper, but may be an economical choice even though the wire diameter is larger for the same resistance. While the applied circuit voltage is intrinsically safe (less than 50V), for corrosion resistance and best electrical safety in the event of the tube being damaged, the wire will ideally be self insulated, either by enamel coating or anodising in the case of aluminium. Alternatively an extruded plastic sheath can be fitted.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended preliminary claims. The disclosures and the descriptions herein are purely illustrative and are not intended to be in any sense limiting.

The invention claimed is:

1. A breathing tube comprising:
 a first inner tube defining a breathing gases passage having a smooth inner surface;
 a second outer tube surrounding said first inner tube and defining a space between said first inner tube and said second outer tube, said space including insulation comprising a substantially stagnant gas;
 a heater located outside said inner surface of said first inner tube and in contact with said first inner tube at a plurality of locations;
 said second outer tube being independently formed and separate from said first inner tube and said first inner tube positioned in a separated arrangement within said second outer tube along a non-tortuous path, and
 wherein a first end of said breathing tube includes a first end connector and a second end of said breathing tube includes a second end connector, said first and second end connectors each separately receives a respective end of each of said inner and outer tubes, each of said inner and outer tubes being maintained in a separated arrangement by said first and second end connectors.

2. A breathing tube as claimed in claim 1, wherein said substantially stagnant gas is at least substantially sealed within said space.

3. A breathing tube as claimed in claim 1, wherein said substantially stagnant gas does not flow through said space at a rate greater than 0.3 L/min.

4. A breathing tube as claimed in claim 1, wherein said heater comprises at least one heater wire wrapped around the outside of said first inner tube.

5. A breathing tube as claimed in claim 1, wherein said heater comprises a heater wire embedded in a wall of said first inner tube.

6. A breathing tube as claimed in claim 1, wherein said heater is a heater wire arranged helically with respect to an axis of said first inner tube.

7. A breathing tube as claimed in claim 6, wherein said helically arranged heater wire is arranged to have a varying helical pitch, along the length of said breathing tube.

8. A breathing tube as claimed in claim 1, wherein said heater is a heater wire arranged parallel with respect to an axis of said first inner tube.

9. A breathing tube as claimed in claim 1, wherein said second outer tube is a corrugated tube.

10. A breathing tube as claimed in claim 1, wherein said insulation in said space further comprises an insulating material such as wool, glass or mineral fibres, insulating gas or fluid, foamed or expanded polymer.

11. A breathing tube as claimed in claim 1, wherein said first inner tube includes at least one helical rib on said smooth inner surface and said at least one helical rib extends at least for the most part in a direction aligned with gasses flow within said first inner tube so that the at least one helical rib does not significantly disrupt gases flow within said first inner tube.

12. A breathing tube as claimed in claim 1, wherein said first inner tube includes at least one helical rib on an outer surface of said first inner tube.

13. A breathing tube as claimed in claim 1, wherein the first inner tube has an inner wall and an outer wall, and wherein said inner wall or said outer wall of said first inner tube further comprises a plurality of ribs arranged about the circumference of said first inner tube and generally aligned with a longitudinal axis of the first inner tube.

14. A breathing tube as claimed in any one of the preceding claims, wherein said first inner tube has an inner diameter of between 3 mm and 15 mm or between 6 mm and 10 mm or between 7 mm and 9 mm.

15. A breathing tube as claimed in claim 1, wherein said second outer tube has an inner diameter of between 15 mm and 30 mm or between 16 mm and 25 mm.

16. A breathing tube as claimed in claim 1, wherein said breathing tube is an inspiratory breathing tube.

17. A breathing tube as claimed in claim 16, wherein said breathing tube is part of a respiratory therapy system for delivering high flow therapy to an infant patient up to 10 L/min.

18. A breathing tube as claimed in claim 16, wherein said breathing tube is part of a respiratory therapy system for delivering high flow therapy to an adult patient up to 60 L/min.

19. A breathing tube as claimed in claim 1, wherein said inner surface of said first inner tube does not include any of:
   a) ribs
   b) corrugations
   c) cavities
   d) bumps, or
   e) features that significantly disrupt gases flow.

20. A breathing tube as claimed in claim 1, wherein the breathing tube is configured to be coupled at one end to a humidifier of a respiratory therapy system for receiving humidified gas and at an opposing end to a patient interface for supplying the humidified gas to a patient through the interface.

* * * * *